US008497017B2

(12) United States Patent
Ohrlander et al.

(10) Patent No.: US 8,497,017 B2
(45) Date of Patent: Jul. 30, 2013

(54) POLYMER MATRIX, USES THEREOF AND A METHOD OF MANUFACTURING THE SAME

(75) Inventors: Mattias Ohrlander, Enskede (SE); Billy Södervall, Markaryd (SE)

(73) Assignee: Bactiguard AB, Stockholm (SE)

( * ) Notice: Subject to any disclaimer, the term of this patent is extended or adjusted under 35 U.S.C. 154(b) by 957 days.

(21) Appl. No.: 12/303,554

(22) PCT Filed: Jun. 5, 2007

(86) PCT No.: PCT/SE2007/000543
§ 371 (c)(1),
(2), (4) Date: Jun. 9, 2009

(87) PCT Pub. No.: WO2007/142579
PCT Pub. Date: Dec. 13, 2007

(65) Prior Publication Data
US 2010/0028436 A1    Feb. 4, 2010

Related U.S. Application Data

(60) Provisional application No. 60/811,305, filed on Jun. 5, 2006.

(51) Int. Cl.
*B32B 15/08* (2006.01)
*B32B 15/18* (2006.01)
*B32B 15/20* (2006.01)
*B32B 18/00* (2006.01)
*B32B 27/08* (2006.01)
*B32B 27/10* (2006.01)
*B32B 27/20* (2006.01)
*B32B 27/28* (2006.01)
*B32B 27/30* (2006.01)
*B32B 27/32* (2006.01)
*B32B 27/34* (2006.01)

(52) U.S. Cl.
USPC ........... 428/328; 428/323; 428/457; 428/458; 428/461; 428/480; 428/481; 428/50; 428/507; 428/515; 106/15.05; 602/41; 602/48; 604/19; 604/264

(58) Field of Classification Search
None
See application file for complete search history.

(56) References Cited

U.S. PATENT DOCUMENTS

| 5,320,908 | A | * | 6/1994 | Sodervall et al. | 428/461 |
|---|---|---|---|---|---|
| 5,322,520 | A | * | 6/1994 | Milder | 604/265 |
| 5,395,651 | A | * | 3/1995 | Sodervall et al. | 427/304 |
| 5,618,265 | A | * | 4/1997 | Myers et al. | 604/20 |
| 5,741,224 | A | * | 4/1998 | Milder et al. | 604/20 |
| 5,747,178 | A | | 5/1998 | Sodervall et al. | |
| 5,759,564 | A | * | 6/1998 | Milder et al. | 424/426 |
| 5,843,186 | A | * | 12/1998 | Christ | 623/6.56 |
| 5,965,204 | A | | 10/1999 | Sodervall et al. | |
| 6,168,633 | B1 | | 1/2001 | Shoher et al. | |
| 6,224,983 | B1 | | 5/2001 | Sodervall et al. | |
| 6,365,220 | B1 | * | 4/2002 | Burrell et al. | 427/2.1 |
| 6,716,895 | B1 | * | 4/2004 | Terry | 523/122 |
| 6,861,570 | B1 | * | 3/2005 | Flick | 602/41 |
| 6,989,157 | B2 | * | 1/2006 | Gillis et al. | 424/618 |
| 7,179,849 | B2 | * | 2/2007 | Terry | 523/122 |
| 7,517,536 | B2 | * | 4/2009 | Ko | 424/443 |
| 7,820,284 | B2 | * | 10/2010 | Terry | 428/323 |
| 8,309,216 | B2 | * | 11/2012 | Ohrlander et al. | 428/328 |
| 8,394,494 | B2 | * | 3/2013 | Ohrlander et al. | 428/328 |
| 2005/0064176 | A1 | * | 3/2005 | Terry | 428/323 |
| 2007/0237946 | A1 | * | 10/2007 | Ohrlander et al. | 428/328 |
| 2009/0123733 | A1 | * | 5/2009 | Ohrlander et al. | 428/328 |
| 2011/0236441 | A1 | * | 9/2011 | Ohrlander et al. | 424/400 |

FOREIGN PATENT DOCUMENTS

| DE | 3830359 | * | 12/1989 |
|---|---|---|---|
| DE | 3830359 A1 | | 12/1989 |
| GB | 1 270 410 | * | 4/1972 |
| JP | 06-016509 | * | 1/1994 |
| JP | 06-016510 | * | 1/1994 |
| WO | WO-97/38648 A1 | | 10/1997 |
| WO | 2005/049699 A2 | | 6/2005 |
| WO | WO-2005/073289 A1 | | 8/2005 |

OTHER PUBLICATIONS

Saygun, O. at al. (2006). "Gold and Gold-Palladium Coated Polypropylene Grafts in a *S. epidermidis* Wound Infection Model," *Journal of Surgical Research* 131:73-79.
International Search Report mailed Sep. 19, 2007, for PCT Application No. PCT/SE2007/000543 filed Jun. 5, 2007, 4 pages.

* cited by examiner

*Primary Examiner* — Vivian Chen
(74) *Attorney, Agent, or Firm* — Morrison & Foerster LLP

(57) ABSTRACT

The present invention relates to a polymer matrix, characterized in that it comprises a) an electron donating constituent and b) metal particles comprising at least one metal chosen from palladium, gold, ruthenium, rhodium, osmium, iridium, and platinum. The polymer matrix makes it possible to improve the biocompatibility and antimicrobial properties of substrates coated with said polymer matrix.

18 Claims, No Drawings

POLYMER MATRIX, USES THEREOF AND A METHOD OF MANUFACTURING THE SAME

CROSS REFERENCE TO RELATED APPLICATIONS

This is a U.S. National Phase patent application of PCT/SE2007/000543, filed Jun. 5, 2007, which claims priority to U.S. Provisional patent application Ser. No. 60/811,305 filed Jun. 5, 2006, all of which are hereby incorporated by reference in the present disclosure in their entirety.

FIELD OF THE INVENTION

The present invention relates to a polymer matrix comprising an electron donating constituent and metal particles. Such a matrix exhibits antimicrobial properties and is biocompatible. Substrates coated at least partly with said polymer matrix have these features. The present invention further relates to a method for manufacturing said polymer matrix. The present invention also relates to use of the polymer matrix. The present invention further relates to articles comprising said polymer matrix.

BACKGROUND

It has always been desirable to improve the antibacterial properties and biocompatibility of certain objects. In particular the desire is to improve antibacterial properties while maintaining other useful properties such as biocompatibility. Over the past 35 years, polymer matrices such as hydrogels have been extremely useful in biomedical and pharmaceutical applications, mainly due to their high water content and rubbery nature which is similar to natural tissue, as well as due to their biocompatibility. Also polymer matrices which are not hydrogels are used within many biomedical and pharmaceutical applications, and it is desired to increase the biocompatibility and antimicrobial properties of those. Examples of known antimicrobial and biocompatible objects for different purposes are outlined below.

U.S. Pat. No. 6,224,983, U.S. Pat. No. 5,965,204, U.S. Pat. No. 5,747,178, U.S. Pat. No. 5,395,651, and U.S. Pat. No. 5,320,908 to Ad Tech Holdings Ltd. disclose articles and methods for preparing articles comprising a layer of silver stabilised by exposure to one or more salts of one or more metals chosen from platinum, palladium, rhodium, iridium, ruthenium and osmium. Examples of the substrate include latex, polystyrene, polyester, polyvinylchloride, polyurethane, ABS polymers, polycarbonate, polyamide, polytetrafluoroethylene, polyimide or synthetic rubber. A latex catheter coated with hydrogel which is further coated with a silver layer is also disclosed.

WO 2005/073289 to Qinetiq Nanomaterials Ltd. discloses fibres made of a polymer composite comprising metal nanoparticles. It is stated that many metals have antimicrobial effects. Antimicrobial fibres are mentioned. One example is a hydrophilic fibre used in antimicrobial wound dressings. Fibres with antimicrobial properties can comprise Ag, Au, Pt, Pd, Ir, Sn, Cu, Sb, Bi or Zn or any combination thereof.

U.S. Pat. No. 6,716,895 to C. R. Bard, Inc. discloses polymer compositions containing colloids of salts of one or more oligodynamic metals. A salt of an oligodynamic metal is reacted with another salt to form a less soluble salt which precipitates as a fine colloid. Examples of metals are silver, platinum, gold, zinc, copper, cerium, gallium, and osmium. An article to be coated is then contacted with a suspension of the poorly soluble colloids. The colloids in the polymer coating can comprise metals salts or metal oxides of oligodynamic metals or a combination thereof.

"Gold and gold-palladium coated polypropylene grafts in a S. epidermidis wound infection model" by Saygun O, Agalar C, Aydinuraz K, Agalar F, Daphan C, Saygun M, Ceken S, Akkus A, and Denkbas E B in J. Surg. Res., 2006 March 131(1):73-9, discloses polypropylene coated with gold and palladium-gold by magnetron sputtering.

BRIEF SUMMARY OF THE PRESENT INVENTION

A problem in the state of the art regarding surfaces is how to improve the biocompatibility and antibacterial properties of certain objects.

The present inventors have provided a solution to the above-mentioned problem by disclosing a polymer matrix, characterized in that it comprises an electron donating constituent and metal particles comprising at least one metal chosen from palladium, gold, ruthenium, rhodium, osmium, iridium, and platinum.

Moreover the present inventors have provided a method of manufacturing the polymer matrix described in the appended claims.

Further embodiments of the present invention are defined in the appended dependent claims which are specifically incorporated by reference herein.

DEFINITIONS

Before the invention is described in detail, it is to be understood that this invention is not limited to the particular configurations, process steps and materials disclosed herein as such configurations, process steps and materials may vary somewhat. It is also to be understood that the terminology employed herein is used for the purpose of describing particular embodiments only and is not intended to be limiting since the scope of the present invention is limited only by the appended claims and equivalents thereof.

It must be noted that, as used in this specification and the appended claims, the singular forms "a", "an" and "the" include plural referents unless the context clearly dictates otherwise.

The following terms are used throughout the description and the claims.

"Air filter" is used herein to denote a device which removes contaminants, often solid particles such as but not limited to chemicals, bacteria, dust, mold, and pollen, from air.

"Antimicrobial" as used herein is the property of preventing, suppressing or eliminating microbial growth.

"Anti thrombogenicity" as used herein is the ability of a substance to inhibit blood clotting.

"Biocompatible" as used herein is the ability of a material to perform with an appropriate host response in a specific application. Examples of properties of a biocompatible object that are within suitable boundaries include the inflammatory response, complement activation, thrombogenicity, protein adsorption, tissue ingrowth, and restenosis.

"Biodegradable polymer" as used herein denotes a polymer that is degraded by hydrolysis and/or a biological system.

"Catheter" is used herein to denote a tube that is intended to be inserted into a body cavity, duct or vessel. Both percutaneous and transcutaneous catheters are encompassed within this definition.

"Chromatography gel" is used herein to denote a polymer matrix intended for use as medium within chromatography.

"Degradable bone fixation plug" is used herein to denote a degradable plug that is used to fix bones in mammals such as a human.

"Degradable bone fixation screw" is used herein to denote a degradable screw that is used to fix bones in mammals such as a human.

"Degradable ligament" is used herein to denote a degradable ligament implant.

"Degradable polymer" is used herein to denote a polymer that can be chemically degraded.

"Dental implant" is used herein to denote an implant intended to be used within dental applications.

"Edible polymer" is used herein to denote a polymer that can be consumed by humans without adverse reactions.

"Endotracheal tube" is used herein to denote a tube for airway management and mechanical ventilation used generally within anaesthesia, intensive care and emergency medicine.

"Environmentally friendly polymer" is used herein to denote a polymer that does not have any major negative impacts on the environment.

"Filter" is used herein to denote a device that is designed to block certain objects or substances while letting others through.

"Graft" is used herein to denote an object intended to be implanted in a mammal such as a human.

"Hydrogel" is used herein to denote a network of crosslinked water-soluble polymer chains.

"Medical device" is used herein to denote a device which is designed to be used in the field of medicine.

"Medical grade polymer" is used herein to denote a polymer that is suitable to use in medical devices with regard to the polymer material and impurities.

"Natural polymer" is used herein to denote a polymer that can be found in nature. A polymer found in nature can be purified by man and still be a natural polymer.

"Nerve guide" is used herein to denote a device which is intended to promote growth or healing of a nerve.

"Polymer matrix" is used herein to denote a matrix of polymers. A polymer matrix can be both cross-linked or non cross-linked.

"Stent" as used herein is an insertable device for placement in a hollow structure of a body, for example an expandable wire mesh or hollow perforated tube.

"Stent graft" as used herein is a stent combined with a tube intended to be implanted in a mammal such as a human.

"Substrate" as used herein is a base-material or object which can be provided with a polymer matrix according to the present invention.

"Tendon implant" as used herein is an implant intended to replace a tendon or support or promote the healing of a tendon.

"Water filter" as used herein denotes a device which removes impurities from water by means of, for example a fine physical barrier and/or chemical processes.

"Wound dressing" as used herein is a therapeutic or protective material applied to a wound.

DETAILED DESCRIPTION OF THE PRESENT INVENTION

The present invention relates to a three-dimensional polymer matrix. The polymer matrix makes it possible to improve the biocompatibility and antimicrobial properties of substrates coated with said polymer matrix.

In one aspect there is described a polymer matrix, characterized in that it comprises an electron donating constituent and metal particles comprising at least one metal chosen from palladium, gold, ruthenium, rhodium, osmium, iridium, and platinum. The metal particles are in one embodiment distributed approximately uniformly in the hydrogel. In another embodiment the metal particles are non-uniformly distributed. As the average particle diameter is from about 10 to about 10000 Å, for example from about 100 to about 600 Å, the particles can be regarded to herein as nanoparticles.

The polymer matrix comprises an electron donating constituent. In one embodiment, the electron donating constituent is a plurality of chemical groups in said polymer matrix. The electron donating chemical groups are in one embodiment be covalently bonded to the polymer matrix. In another embodiment the electron donating chemical groups are added as a further substance to the polymer matrix. Thus the electron donating groups are in one embodiment non-covalently bonded to the polymer matrix. In yet another embodiment the electron donating groups are present in a solvent in the polymer matrix without being bound to the polymer matrix.

Examples of electron donating groups include complex bound metals such as, but not limited to Ag, Al, Zn, Cu, and Fe. Further non-limiting examples of electron donating groups in the polymer matrix are primary, secondary and tertiary amines, oxygen containing groups, and chlorine containing groups. Other examples of electron donating constituents are Lewis bases.

In one embodiment the electron donating constituent is a system of conjugated pi orbitals. One example of a conjugated system is a system of atoms covalently bonded with alternating single and multiple (e.g. double) bonds (e.g., C=C—C=C—C) in a molecule of an organic compound.

In another embodiment the electron donating constituent are polythiophenes. Polythiophenes are suitable for use in the present invention.

In another embodiment the electron donating constituent is a conducting material which is electrically connected to an electron donating function. For instance a metal connected to a power supply.

In an alternative embodiment, the electron donating constituent is particles comprising a metal which is less noble than the at least one metal in the metal particles in the polymer matrix. That is, the metal in the electron donating constituent should be less noble than the other metal particles in the polymer matrix.

In one embodiment the electron donating constituent is particles comprising at least one metal chosen from silver, copper, and zinc. In one particular embodiment particles comprising silver are used.

Also encompassed, as an electron donating constituent, is a combination of electron donating chemical groups and metal particles.

The material of the polymer matrix is one or more materials chosen from large group or a combination thereof. The polymer matrix is built up of polymers including for example a cross-linked hydrogel, a non-crosslinked polymer solution, or a polymer gel. Hydrogels are water-swollen networks or crosslinked structures composed of hydrophilic homopolymers or copolymers. They are rendered insoluble due to the presence of chemical, i.e. covalent or ionic crosslinks or physical crosslinks. Non-limiting examples of the latter are entanglements, crystallites, and hydrogen-bonded structures. The crosslinks provide the network structure and physical integrity. They can be neutral or ionic hydrogels based on the type of charges of their pendent groups. They can also be classified as amorphous, semi crystalline, hydrogen-bonded structures, super molecular structures, or hydro colloidal aggregates.

The polymer matrix according to the present invention is in one embodiment degradable. In an alternative embodiment the polymer matrix is non-degradable. The polymer matrix according to the present invention is in one embodiment made of a synthetic material. The polymer matrix according to the present invention is in one embodiment hydrolytically degradable or hydrolytically biodegradable. In one embodiment the polymer matrix according to the present invention comprises crosslinked hydrophilic polymers.

Examples of classes of polymers which can be used as a polymer matrix according to the present invention include hydrophilic acrylics, peptides, dendrimers, star-polymers, aliphatic polymers, natural polymers, synthetic polymers, anionic polymers, cationic polymers, neutral polymers, and synthetic polymers.

Examples of polymers which are suitable for the manufacture of the polymer matrix according to the present invention include polyanionic polysaccharides, carboxymethyl cellulose, carboxymethyl amylose, chondroitin-6-sulfate, dermatin sulfate, heparin, heparin sulfate, poly(hydroxyethyl methylacrylate), collagen, fibrinogen, albumin, fibrin, acrylamide, hydroxypropyl methacrylamide-based copolymers, polyacrylamide, poly(N-isopropyl acrylamide) (pNIPAAm), polyvinylpyrrolidone, poly(vinyl alcohol) (PVA), poly(ethylene glycol) (PEG), poly(methacrylic acid-g-ethylene glycol), poly(N-2-hydroxypropyl methacrylamide), poly(glycolic acid), poly(glycolic acid) (PGA), poly(lactic acid) (PLA), chitosan, poly(2-hydroxyethylmethacrylate) (HEMA), polyphazene, phosphorylcholine, hyaluronic acid (HA), HEMA, hydroxyethyl methacrylate (HEMA), methylene-bis-acrylamide (MBAAm), poly(acrylic acid) (PAAc), polyacrylamide (PAAm), polyacrylonitrile (PAN), poly(butylene oxide) (PBO), polycaprolactone (PCL), poly(ethylene imine) (PEI), poly(ethylene oxide) (PEO), poly(ethyl methacrylate) (PEMA), propylene fumarate (PF), poly(glucosylethyl methacrylate) (PGEMA), poly(hydroxy butyrate) (PHB), poly(hydroxyethyl methacrylate) (PHEMA), poly(hydroxypropyl methacrylamide) (PHPMA), poly(lactic acid) (PLA), poly(lactic-co-glycolic acid) (PLGA), poly(methyl methacrylate) (PMMA), poly(N-vinyl pyrrolidone) (PNVP), poly(propylene oxide) (PPO), poly(vinyl alcohol) (PVA), poly(vinyl acetate) (PVAc), poly(vinyl amine), pectin, carrageenan, chondroitin sulfate, dextran sulfate, chitosan, polylysine, collagen, gelatin, carboxymethyl chitin, fibrin, dextran, agarose, pullulan, polyesters, PEG-PLA-PEG, PEG-PLGA-PEG, PEG-PCL-PEG, PLA-PEG-PLA, poly(PF-co-EG), poly(PEG/PBO-terephthalate), PEG-bis-(PLA-acrylate), PEG6CDs, PEG-g-poly(AAm-co-vinlyamine), poly(NIPAAm-co-AAc), poly(NIPAAm-co-EMA), PVAc/PVA, PNVP, poly(MMA-co-HEMA), poly(AN-co-allyl sulfonate), poly(biscarboxy-phenoxy-phosphazene), poly(GEMA-sulfate), poly(PEG-co-peptides), alginate-g-(PEO-PPO-PEO), poly(PLGA-co-serine), collagen-acrylate, alginate-acrylate, poly(HPMA-g-peptide), HA-g-NIPAAm, poly(vinyl methyl ether) (PVME), and polyethylenimine or any combination or any copolymer thereof.

Examples of degradable polymers suitable for use in the present invention include: poly(amino acids), poly(anhydride), poly(caprolactone), poly(lactic acid), poly(lactic-glycolic acid), poly(hydroxybutyrate), poly(orthoesters), and poly(trimethylene carbonate).

In one embodiment the polymers for use in the manufacture of the polymer matrix in the present invention include PEG (polyethylene glycol), PVP (polyvinylpyrrolidone), PAA (polyacrylic acid), polyurethane, dextran sulphate, heparin, collagen, poly(vinylmethylether), and poly(hydroxyethylmethacrylate).

Optionally there are other non-metal particles present in the polymer matrix. Optionally the polymer matrix comprises additives such as those which are well known to a person skilled in the art of polymer matrices and hydrogels.

The polymer matrix according to the invention may be applied to a substrate. The substrate is partly or alternatively completely coated with the polymer matrix. A substrate is in one embodiment coated with several different types of polymer matrices.

A polymer matrix and especially a hydrogel can be coated on a substrate according to well-known methods. For an overview of polymer matrices and hydrogels, see for instance R. Langer et al., AIChE Journal, vol. 49 (2003), pp 2990-3006.

The polymer matrix according to the invention can be coated on a large variety of substrates. Examples of substrates include latex, vinyl, polymers comprising vinyl groups, polyurethane urea, silicone, polyvinylchloride, polypropylene, styrene, polyurethane, polyester, copolymerisates of ethylene vinyl acetate, polystyrene, polycarbonate, polyethylene, polyacrylate, polymethacrylate, acrylonitrile butadiene styrene, polyamide, polyimide polytetrafluoroethylene, polyparaphenyleneterephthalamide, a natural polymer, a degradable polymer, an edible polymer, a biodegradable polymer, an environmental friendly polymer, a medical grade polymer or a combination thereof.

When the substrate is a polymer it can act as the polymer matrix according the present invention. Thus all polymeric materials mentioned above for the substrate may also be the polymer matrix according to the present invention.

Substrates include stainless steel, medical grade steel, titanium, medical grade titanium, cobalt, chromium and aluminium or mixtures thereof.

Alternatively substrates include glass, minerals, zeolites, stone and ceramics or a combination thereof.

Other substrates according to the present invention are chosen from paper, wood, woven fibres, fibres, cellulose fibres, leather, carbon, carbon fibres, graphite or a combination thereof.

A person skilled in the art can in the light of this description apply a hydrogel on the above mentioned substrates.

The method of manufacturing a polymer matrix according to the invention comprises exposing the polymer matrix to at least one dispersion of the desired particles. The polymer matrix is either commercially available or is manufactured according to known methods. A person skilled in the art knows how to prepare a polymer matrix such as a hydrogel which can be used in the present invention. PEG-based, PAA-based and PVP-based hydrogels are examples of commercially available hydrogels that can be used in the present invention.

The suspension of metal particles can be manufactured in several ways. In one embodiment the suspension of metal particles is made using an aqueous solution of a metal salt which is reduced under conditions such that metal particles of a desired size are formed. Mixing a suitable amount of metal salt, reducing agent and stabilising agent achieves this. Such a suspension comprises a metal salt, and a reduction agent that reduces the metal-containing salt to elemental metal. The reduction agent must be present in an amount sufficient to accomplish the chemical reduction. Acceptable reduction agents include formaldehyde, hydrazine sulphate, hydrazine hydroxide, and hypophosphoric acid. In one embodiment of the present invention a reduction agent is present in an amount of about 0.001 millilitres per litre of solution. Too high a concentration of the reduction agent causes deposition of metal throughout the solution and on the container walls, while too low a concentration may result in an insufficient formation of metal on the substrate. A person skilled in the art can determine the desired amount of reduction agent. Another component of the dispersion of this embodiment is a control agent that is present in an amount sufficient to slow the deposition reaction to prevent the reduced metal from precipitating directly from solution as a fine metallic powder, or precipitating onto the walls of the container. Operable control agents include inverted sugar, also known as invertose, succinic acid, sodium citrate, sodium acetate, sodium hydroxide, potassium hydroxide, sodium tartrate, potassium tartrate, and ammonia. In one embodiment the deposition control agent is present in an amount of about 0.05 grams per litre of solution.

The concentrations of the reduction agent and the control agent is adjusted as necessary to achieve the desired results, depending upon the substrate material, if any, the thickness of the polymer matrix desired, and the concentration of metal in the solution.

In an alternative embodiment a commercially available colloidal suspension of metal particles is used. Metal particles of the desired composition are used to make the suspension. For instance a commercially available suspension of gold and palladium particles from the company Johnson Matthey can be used in the present invention.

In one embodiment the suspension or suspensions of metal particles is made by diluting a commercially available concentrated colloidal suspension of metal particles comprising the desired metal with demineralised water. The polymer matrix is treated with the suspension for a period of time from about a few seconds to about a few minutes or longer.

In one embodiment the polymer matrix is exposed to a first suspension which comprises metal particles comprising silver and subsequently to a second suspension which comprises metal particles comprising at least one metal chosen from palladium, gold, ruthenium, rhodium, osmium, iridium, and platinum.

In an alternative embodiment the polymer matrix is exposed to one suspension comprising metal particles comprising silver and metal particles comprising at least one metal chosen from palladium, gold, ruthenium, rhodium, osmium, iridium, and platinum.

In one embodiment the amount of metal particles comprising at least one metal chosen from palladium, gold, ruthenium, rhodium, osmium, iridium, and platinum in the polymer matrix is from about 0.1 µg to about 1000000 µg metal per 1 g polymer matrix. In another embodiment the amount of metal particles is from about 1 µg to about 100000 µg metal per 1 g polymer matrix. In yet another embodiment the amount of metal particles is from about 1 µg to about 800 µg metal per 1 g polymer matrix. The weight of the polymer matrix includes the solvent in the polymer matrix and the polymer of the matrix as well as optional additives in the polymer matrix. In one embodiment the amount of optional metal particles acting as electron donating constituent is from about 0.1 µg to about 100000 µg metal per 1 g polymer matrix. In another embodiment the amount of optional metal particles acting as electron donating constituent is from about 1 µg to about 10000 µg metal per 1 g polymer matrix. In yet another embodiment the amount of optional metal particles acting as electron donating constituent is from about 1 µg to about 800 µg metal per 1 g polymer matrix.

In one embodiment the polymer matrix is exposed to a primer before exposing it to the at least one suspension comprising metal particles. One example of a primer is a solution comprising $Sn^{2+}$ ions at pH 1-4, by which the polymer matrix is treated during 2-60 minutes.

In one embodiment a pre-treatment is used before the primer. Examples of pre-treatment include treatment with plasma treatment, irradiation with electrons, and irradiation with gamma irradiation. The pre-treatment can optionally comprise adding functional chemical groups covalently or non-covalently bound.

The polymer matrix is used for diverse applications in many fields. Examples include use for the manufacture of a medical device, a catheter, an endotracheal tube, a stent, a graft, a stent graft, a chromatography gel, a filter, an air filter, a water filter, a wound dressing, a mesh, a degradable bone fixation plug or screw, a degradable ligament implant, a tendon implant, a dental implant, and a nerve guide. Further example of articles where the polymer matrix according to the present invention can be used include a medical instrument, a disposable article, a medical disposable article, a contact lens, a pacemaker, a pacemaker electrode, a stent, a dental implant, a rupture net, a rupture mesh, a blood centrifuge equipment, a surgical instrument, a glove, a blood bag, an artificial heart valve, a central venous catheter, a peripheral venous catheter, a vascular port, a haemodialysis equipment, a peritoneal dialysis equipment, a plasmapheresis device, an inhalation drug delivery device, a vascular graft, an arterial graft, a cardiac assist device, a wound dressing, an intermittent catheter, an ECG electrode, a peripheral stent, a bone replacing implant, an orthopaedic implant, an orthopaedic device, a tissue replacing implant, an intraocular lens, a suture, a needle, a drug delivery device, an endotracheal tube, a shunt, a drain, a suction device, and a hearing aid device. The polymer matrix according to the present invention can be used as a component in the above-mentioned objects and can be used during manufacture of the above-mentioned objects.

In a medical device the polymer matrix according to the present invention can be used where a polymer matrix is required for certain purposes such as for increasing the biocompatibility, reducing inflammatory response, reducing complement activation, reducing thrombogenicity, reducing protein adsorption, enhancing tissue ingrowth and wherein the medical device at the same time exhibits antimicrobial properties. Other examples are polymer matrixes in a medical device that holds a drug that can be released to the surrounding or a polymer matrix that interacts with a biological system.

A polymer matrix such as a hydrogel or a non-hydrogel can according to the present invention be applied on the surface of a catheter in order to increase biocompatibility and/or increase lubricious properties or adjust other properties relevant for catheters and at the same time achieving antimicrobial properties. Another approach is to deposit the metal particles directly in the polymer matrix of the catheter material in order to obtain antimicrobial properties. In the latter case the catheter itself is the polymer matrix according to the present invention.

A polymer matrix according to the present invention can be applied on the surface of endotracheal tubes in order to increase biocompatibility and/or increase lubricious properties or adjust other properties that are relevant for tracheal tubes and which at the same time exhibits antimicrobial properties. Another approach is to deposit the metal particles directly in the polymer matrix of the endotracheal tube material in order to achieve antimicrobial properties and the other desired properties. Thus the endotracheal tube itself can be the polymer matrix according to the invention.

A polymer matrix can be applied on the surface of a stent in order to increase biocompatibility and/or decrease restenosis and to adjust other properties that are important for a stent, wherein the stent at the same time has antimicrobial properties. If the stent is made of a polymer or coated by a polymer, an alternative approach is to deposit the metal particles in the polymer matrix of the stent material or in the polymer coated stent in order to obtain antimicrobial properties. In the latter case the polymer matrix according to the invention is the stent material and/or the coating of the stent.

A polymer matrix according to the present invention can be applied on the surface of a graft in order to increase biocompatibility and/or decrease restenosis or adjust other properties that are relevant for grafts, while the graft at the same time has antimicrobial properties. If the graft is made of a polymer or coated by a polymer, another approach is to add the metal particles directly in the polymer matrix of the graft material or in the polymer coated graft in order to get antimicrobial properties. Thus the material of the graft is in one embodiment the polymer matrix of the present invention. Also encompassed are grafts where only the outer layer has the electron donating constituent and the metal particles according to the present invention.

Metal particles can be deposited in a chromatography gel material for the purpose of filtering or separating and analysing species that are sensitive towards the deposited metal particles. Examples include studying antimicrobial properties by letting microbes pass the gel and another example includes using the deposited metal particles for catalytic purposes.

The polymer matrix according to the present invention can be used in filters such as for instance air filters and water filters. As an example a polymer matrix can be applied on the surface of a filter material and metal particles are deposited in the polymer matrix. If the filter is made of a polymer or coated by a polymer, another approach is to deposit the metal particles directly in the polymer matrix of the filter material or in the polymer in the coating of the filter in order to achieve the desired properties.

The polymer matrix according to the present invention can be used for wound dressings. A silicone based polymer matrix is treated with metal particles in such a way that the metal particles can diffuse in to the polymer matrix. Another way is to treat the silicone pre-crosslinked polymers with metal particles with subsequent crosslinking. The incorporated metal particles can act as antimicrobial agents by slow release.

The polymer matrix according to the present invention can be used for catheters. Examples include a Foley catheter of latex with a PEG based polymer matrix applied on the catheter surface for lubricious purposes. The metal particles are deposited in the lubricious coating. Such a catheter will exhibit antimicrobial properties together with excellent biocompatibility. Another example is a Foley catheter of silicone with a polyacrylic based polymer matrix applied on the catheter surface for lubricious purposes. The metal particles are deposited in the lubricious coating and the catheter shows antimicrobial and biocompatible properties.

Further examples of catheters include CVC, IV-catheters, and peripheral catheters. A polymer matrix containing heparin can be applied on the catheter surface. The metal particles can be deposited in the polymer matrix giving biocompatibility and antimicrobial properties.

A mesh intended to be implanted in a mammal such as a human can be coated with a polymer matrix according to the present invention, or if the mesh is made of a polymeric material, the polymeric material is in one embodiment the polymer matrix according to the present invention. Such a mesh will benefit from enhanced biocompatibility and antimicrobial properties.

A degradable bone fixation plug or screw and a degradable ligament implant may be coated with a polymer matrix according to the present invention. If such a device is made of a polymeric material the polymeric material itself may be the polymer matrix according to the present invention.

The polymer matrix according to the present invention can be used in the manufacture of a tendon implant. The tendon implant can be coated with a polymer matrix according to the present invention or alternatively if the tendon implant is made of a polymeric material the polymeric material can be the polymer matrix according to the present invention.

The polymer matrix according to the present invention can be used in the manufacture of a dental implant. The dental implant can be partly or completely coated with a polymer matrix according to the present invention or alternatively, if the dental implant is made of a polymeric material the polymeric material can be the polymer matrix according to the present invention.

The polymer matrix according to the present invention can be used in the manufacture of a nerve guide intended to be implanted in mammals or humans to promote nerve growth along it. The tendon implant can be coated with a polymer matrix according to the present invention or alternatively if the tendon implant is made of a polymeric material the polymeric material can be the polymer matrix according to the present invention.

In one embodiment at least one layer of one or several different materials are applied on the matrix according to the present invention. All suitable surface treatments can be used to treat an article coated according to the present invention. Many different materials can be applied to an article which is coated according to the present invention. Examples include heparin.

The polymer matrix of the present invention is biocompatible and exhibits antibacterial properties, which means that it can be used without toxic consequences in applications requiring contact with mammalian tissue. Further advantages are that the particles can be incorporated in the polymer matrix and do not dissolve rapidly. The present invention thus makes it possible to manufacture a coating with slow release properties.

The embodiments of the present invention combine the excellent biocompatibility of polymer matrices such as hydrogels with the desired antimicrobial properties.

Other features of the invention and their associated advantages will be evident to a person skilled in the art upon reading the description and the examples.

It is to be understood that this invention is not limited to the particular embodiments shown here. The following examples are provided for illustrative purposes and are not intended to limit the scope of the invention since the scope of the present invention is limited only by the appended claims and equivalents thereof.

EXAMPLES

Example 1

Coating Latex with Hydrogel According to the Present Invention

Latex coated with a PEG-based (polyethylene glycol based) polymer matrix was used. This PEG-based polymer matrix is a hydrogel. The PEG based hydrogel was manufactured by letting the polymer substrate swell in a solvent and thereafter adding isocyanate, polyurethane polyol, PEG, and an initiator, where after the mixture was allowed to react so that an interpenetrating polymer network (IPN) was formed. The average thickness of the polymer matrix on the latex substrate was about 50-200 µm. The coated substrate was cleaned in demineralised water before dipping in a solution containing 0.01 g/l of stannous ions ($Sn^{2+}$) at a pH of 2.5. After rinsing the substrate was immersed in two deposition solutions comprising 0.005 g/l of silver ions, 0.02 ml/l ammonia, 0.05 g/l potassium hydroxide and 0.05 ml/l hypophosphoric acid for 5 min at room temperature. This resulted in a polymer matrix with an amount of silver particles corresponding to 2.86 µg/cm². (The amount of silver particles and metal particles is given in µg/cm² because the hydrogel was rather thin. The amounts may of course be recalculated as µg/cm³ or equivalent.) After rinsing it was immersed in a suspension of particles comprising 23% palladium and 77% gold. The suspension of metal particles was manufactured by reducing a gold and palladium salt respectively with a reducing agent and stabilising the suspension with a stabilising agent. The substrate was subsequently rinsed in demineralised water and dried. The amount of palladium-gold particles in the hydrogel corresponded to 0.62 µg/cm².

Example 2

Coating Latex with Hydrogel According to the Present Invention

A matrix coated substrate as in example 1 was cleaned in demineralised water and then rinsed in demineralised water before dipping in a solution containing 0.01 g/l of the stannous ion at a pH of 2.5. After rinsing the substrate was immersed in a solution containing 0.005 g/l of silver ions, 0.02 ml/l ammonia, 0.05 g/l potassium hydroxide and 0.05 ml/l hypophosphoric acid for 1 min at room temperature. This gave a surface with an amount of silver corresponding to 1.74 µg/cm². After rinsing it was immersed in a particle suspension comprising 0.005 g/l palladium and 0.002 g/l gold particles. The applied amount of palladium and gold particles corresponded to 0.62 µg/cm².

Example 3

Growth of Bacteria on Substrates Having a Polymer Matrix According to the Present Invention A polymer matrix was coated on latex tubes with an outer diameter of 6 mm following the method outlined in example 1. The particles comprised 95% palladium and 5% gold. The following samples were tested for their ability to suppress bacterial growth:
1) (comparative) uncoated latex tubes,
2) (comparative) latex tubes without hydrogel with a deposited layer of silver covered with metal particles comprising palladium and gold,
3) (according to the present invention) latex tubes coated with a hydrogel comprising silver particles corresponding to 1.74 µg/cm², and particles of palladium, 0.62 µg/cm².
4) (according to the present invention) same as 3 but a more metal silver particles, namely 2.86 µg/cm² of silver particles and 0.62 µg/cm² of palladium particles.

Samples were placed into universals. Samples were provided in triplicates for each test group. 10 ml of growth medium containing inoculated *E. coli* (roughly $10^5$ CFU/ml) was added to each universal and they were incubated horizontally with gentle shaking at 37° C. for 4 hours (a first test group) or 24 hours (a second test group).

After 4 and 24 hours, respectively, the universals were removed from incubation. The samples were removed and CFU (colony forming unit) counts were done from each universal by carrying out 10-fold dilutions in sterile distilled water and plating 100 µl onto a third of a nutrient agar plate. These plates were incubated for 16-24 hours at 37° C. and the colonies counted. The log CFU/ml versus a control was calculated and is shown in Table 1.

TABLE 1

| | Average log cult. CFU/ml |
|---|---|
| | 4 hours incubation: |
| 1 | 7.8 |
| 2 | 3.2 |
| 3 | 0 |
| 4 | 0 |
| | 24 Hours incubation: |
| 1 | 8.3 |
| 2 | 8.2 |
| 3 | 2.3 |
| 4 | 2.0 |

It can be seen that the coating according to the present invention (3 and 4) clearly shows an improved effect regarding suppression of bacterial growth compared to the uncoated latex tubes (1) and the comparative latex tubes coated with silver and particles of palladium and gold (2).

Also, the log CFU per centimetre of latex tube was calculated for the different samples. The results are given in table 2.

TABLE 2

| | Average log CFU/cm |
|---|---|
| | 4 hours incubation: |
| 1 | 5.6 |
| 2 | 4.0 |
| 3 | 0 |
| 4 | 2.5 |
| | 24 hours incubation: |
| 1 | 6.4 |
| 2 | 6.5 |
| 3 | 4.2 |
| 4 | 2.6 |

By reviewing the log CFU/cm it can be seen that the coating according to the present invention (3 and 4) shows an improved effect regarding suppression of bacterial growth compared to the uncoated latex tubes (1) and the comparative latex tubes with silver and particles of palladium and gold (2).

Example 4

Antimicrobial Effect of a Polymer Matrix According to the Present Invention

A medical grade silicone tubing (Pt cured) was used as a base for the coating. The silicone tube was coated with polyelectrolytes. First the silicone tube was immersed in a solution of polyethylenimine (Polymin) and then it was immersed in a solution of dextran sulphate. This gave a silicon tube with a coating of polyelectrolytes. The coated silicone tube was cleaned in demineralised water before dipping in a solution containing 0.01 g/l of stannous ions ($Sn^{2+}$) at a pH of 2.5. After rinsing, the silicone tube was immersed in two deposition solutions comprising 0.005 g/l of silver ions, 0.02 ml/l ammonia, 0.05 g/l potassium hydroxide and 0.05 ml/l hypophosphoric acid for 5 min at room temperature. This resulted in a polymer matrix with an amount of silver particles corresponding to 2.86 µg/cm². (The amount of silver particles and metal particles is given in µg/cm² because the polymer coating was rather thin. The amounts may of course be recalculated as µg/cm³ or equivalent.) After rinsing it was immersed in a suspension of particles comprising 23% palladium and 77% gold. The suspension of metal particles was manufactured by reducing a gold and palladium salt respectively with a reducing agent and stabilising the suspension with a stabilising agent. The substrate was subsequently rinsed in demineralised water and dried. The amount of palladium-gold particles in the polymer coating corresponded to 0.62 µg/cm².

Also control samples were manufactured without the metal but with the polymer coating on the silicone tube.

The antimicrobial effect of the samples were tested in an in vitro model. The samples were placed into universals. The samples were provided in triplicates for each test group. 10 ml of artificial urine containing inoculated *E. coli* was added to each universal and they were incubated horizontally with gentle shaking at 37° C. for 4 hours (a first test group) or 24 hours (a second test group).

After 4 and 24 hours, respectively, the universals were removed from incubation. The samples were removed and CFU (colony forming unit) counts were done from each universal by carrying out 10-fold dilutions in sterile distilled water and plating 100 µl onto a third of a nutrient agar plate. These plates were incubated for 16-24 hours at 37° C. and the colonies counted.

The antimicrobial effect from each sample was estimated by analysing the artificial urine solutions as well as the sample surfaces. The log CFU/ml versus a control was calculated and also the log CFU per centimetre of silicone tube was calculated for the different samples. The results are outlined in table 3.

TABLE 3

| Sample | Av. Log CFU/ml 4 h | Av. Log CFU/ml 24 h | Av. Log CFU/cm 4 h | Av. Log CFU/cm 24 h |
|---|---|---|---|---|
| Silicone tube + polymer coating (comparative) | 7.7 | 8.1 | 5.28 | 5.7 |
| Silicone tube + polymer coating including metal particles (according to the invention) | 0.0 | 3.4 | 0.4 | 2.4 |

It can be concluded that the coating according to the present invention has an antimicrobial effect and suppresses bacterial growth both regarding the surface of the coated article and regarding the surrounding media of the coated article.

Example 5

A polymer Matrix According to the Present Invention Comprising Heparin

A medical grade silicone tubing (Pt cured) was used as a base. The silicone tube was first plasma treated. Thereafter it was treated with a heparin primer layer. The heparin treatments in this example were performed following the method outlined in Wirsén, Ohrlander and Albertsson in Biomaterials vol. 17, no 19, 1881-1889, (1996). The coated silicone tubes were cleaned in demineralised water before dipping in a solution containing 0.01 g/l of stannous ions ($Sn^{2+}$). After rinsing, the silicone tube was immersed in two deposition solutions comprising 0.005 g/l of silver ions, 0.02 ml/l ammonia, 0.05 g/l potassium hydroxide and 0.05 ml/l hypophosphoric acid for 5 min at room temperature. This resulted in an amount of silver particles corresponding to 2.86 µg/cm². (The amount of silver particles and metal particles is given in µg/cm² because the layer on the sample was rather thin. The amounts may of course be recalculated as µg/cm³ or equivalent.) After rinsing it was immersed in a suspension of particles comprising 23% palladium and 77% gold. The suspension of metal particles was manufactured by reducing a gold and palladium salt respectively with a reducing agent and stabilising the suspension with a stabilising agent. The substrate was subsequently rinsed in demineralised water and dried. The amount of palladium-gold particles in the polymer coating corresponded to 0.62 µg/cm².

After the coating with silver, gold and palladium, samples were subjected to heparinization with 3 and 4 layers respectively. The heparinization followed the method outlined in Wirsén, Ohrlander and Albertsson in Biomaterials vol. 17, no 19, 1881-1889, (1996).

The anti-bacterial properties of the samples were measured as in example 4. The tests included a) inoculum, b) a control sample, c) uncoated silicone, d) heparin coated silicone, 3 layers (as described above according to the invention), and e) heparin coated silicone, 4 layers (as desribed above according to the invention). The log CFU/ml versus a control was calculated and also the log CFU per centimetre of silicone tube was calculated for the different samples.

| Sample | Av. Log CFU/ml 4 h | Av. Log CFU/ml 24 h | Av. Log CFU/cm 4 h | Av. Log CFU/cm 24 h |
|---|---|---|---|---|
| Inoculum | 5.2 | NA | 5.2 | NA |
| Control | 7.6 | NA | 8.0 | NA |
| Uncoated silicone | 7.2 | 4.1 | 7.9 | 6.0 |
| Heparin coated silicone (4 layers) | 3.9 | 2.0 | NM | NM |
| Heparin coated silicone (3 layers) | 3.6 | 0.7 | NM | NM |

NA not applicable
NM not measured

It can be concluded that the surfaces exhibit a reduction of *E. coli*. The surfaces are both antimicrobial and biocompatible.

The invention claimed is:

1. A polymer matrix, characterized in that it comprises
   a) an electron donating constituent and
   b) metal particles comprising palladium and gold,
   wherein the metal particles have an average particle diameter of from about 10 to about 10000 Å and wherein said electron donating constituent are particles comprising silver.

2. The polymer matrix according to claim 1, wherein said particles comprising silver further comprise copper or zinc.

3. The polymer matrix according to claim 1, wherein said polymer matrix is a hydrogel.

4. The polymer matrix according to claim 1, wherein said polymer matrix comprises at least one component selected from the group consisting of:
   acrylamide,
   agarose,
   albumin,
   alginate-acrylate,
   alginate-(polyethylene oxide-polypropylene oxide-polyethylene oxide),
   carboxymethyl amylose,
   carboxymethyl cellulose,
   carboxymethyl chitin, carrageenan,
chitosan,
chondroitin sulfate,
chondroitin-6-sulfate,
collagen,
collagen-acrylate,
dermatin sulfate,
dextran,
dextran sulfate,
fibrin,
fibrinogen,
gelatin,
heparin,
heparin sulfate,
hyaluronic acid (HA),
hyaluronic acid-g-N-isopropyl acrylamide (HA-g-NIPAAm),
hydroxyethyl methacrylate (HEMA),
hydroxypropyl methacrylamide-based copolymers,
methylene-bis-acrylamide (MBAAm),
pectin,
phosphorylcholine,
poly(2-hydroxyethyl methacrylate),
polyacrylamide (PAAm),
poly(acrylic acid) (PAAc),
polyacrylonitrile (PAN),
poly(acrylonitrile-co-allyl sulfonate),
polyanionic polysaccharides,
poly(biscarboxy-phenoxyphosphazene),
poly(butylene oxide) (PBO),
polycaprolactone (PCL),
polyesters,
poly(ethyl methacrylate) (PEMA),
poly(ethylene glycol) (PEG),
poly(ethylene glycol)-6CDs (PEG6CDs),
polyethylene glycol-bis-(polylactic acid-acrylate) (PEG-bis-PLA-acrylate),
polyethylene glycol-g-poly(acrylamide-co-vinylamine),
polyethylene glycol-polycaprolactone-polyethylene glycol (PEG-PCL-PEG),
polyethylene glycol-polylactic acid-polyethylene glycol (PEG-PLA-PEG),
polyethylene glycol-polylactic-co-glycolic acid-polyethylene glycol (PEG-PLGA-PEG),
poly(ethylene imine) (PEI),
poly(ethylene oxide) (PEO),
poly(glucosylethyl methacrylate) (PGEMA),
poly(glucosylethyl methacrylate sulfate),
poly(glycolic acid) (PGA),
poly(hydroxypropyl methacrylamide-g-peptide) (poly(HPMA-g-peptide),
poly(hydroxy butyrate) (PHB),
poly(hydroxyethyl methacrylate) (PHEMA),
poly(hydroxyethyl methylacrylate),
poly(hydroxypropyl methacrylamide) (PHPMA),
poly(lactic acid) (PLA),
poly(lactic-co-glycolic acid) (PLGA),
poly(lactic-co-glycolic acid-co-serine),
polylactic acid-polyethylene glycol-polylactic acid (PLA-PEG-PLA),
polylysine,
poly(methacrylic acid-g-ethylene glycol),
poly(methyl methacrylate) (PMMA),
poly(methyl methacrylate-co-hydroxyethyl methacrylate),
poly(N-2-hydroxypropyl methacrylamide),
poly(N-isopropyl acrylamide-co-acrylic acid),
poly(N-isopropyl acrylamide-co-ethylmethacrylate),
poly(N-isopropyl acrylamide) (pNIPAAm),
poly(N-vinyl pyrrolidone) (PNVP),
poly(ethylene glycol/butylene oxide-terephthalate),
poly(ethylene glycol-co-peptides),
poly(propylene fumarate-co-ethylene glycol),
polyphazene,
poly(propylene oxide) (PPO),
poly(vinyl acetate) (PVAc),
poly(vinyl alcohol) (PVA),
poly(vinyl amine),
poly(vinyl methyl ether) (PVME),
polyvinyl pyrrolidone,
propylene fumarate (PF), and
pullulan, or a combination thereof.

5. The polymer matrix according to claim 1, wherein said polymer matrix comprises at least one component selected from the group consisting of poly(amino acids), poly(anhydride), poly(caprolactone), poly(lactic acid), poly(lactic-glycolic acid), poly(hydroxybutyrate), poly(orthoesters), and poly(trimethylene carbonate).

6. The polymer matrix according to claim 1, wherein said polymer matrix comprises at least one component selected from the group consisting of latex, vinyl, polymers comprising vinyl groups, polyurethane urea, silicone, polyvinylchloride, polypropylene, styrene, polyurethane, polyester, copolymerisates of ethylene vinyl acetate, polystyrene, polycarbonate, polyethylene, polyacrylate, polymethacrylate, acrylonitrile butadiene styrene, polyamide, polyimide polytetrafluoroethylene, and polyparaphenyleneterephthalamide, or any combination thereof.

7. The polymer matrix according to claim 1, wherein said polymer matrix comprises at least one component selected from the group consisting of PEG, polyvinyl pyrrolidone, poly(urethane), dextran sulphate, heparin, collagen, poly(vinylmethylether), and poly(hydroxyethylmethacrylate).

8. A substrate at least partly coated with a polymer matrix according to claim 1.

9. The substrate according to claim 8, wherein the substrate comprises a material selected from the group consisting of stainless steel, medical grade steel, titanium, medical grade titanium, cobalt, chromium and aluminium or mixtures thereof.

10. The substrate according to claim 8, wherein the substrate comprises a material selected from the group consisting of glass, minerals, zeolites, stone and ceramics or a combination thereof.

11. The substrate according to claim 8, wherein the substrate comprises a material selected from the group consisting of paper, wood, woven fibres, fibres, cellulose fibres, leather, carbon, carbon fibres, graphite or a combination thereof.

12. A method of manufacturing a polymer matrix according to claim 1, comprising exposing said polymer matrix to at least one suspension comprising metal particles.

13. The method according to claim 12 wherein said polymer matrix is exposed to a first suspension comprising metal particles and subsequently exposed to a second suspension comprising metal particles, wherein said metal particles of said first suspension comprise silver, and said metal particles of said second suspension comprise palladium and gold.

14. The method according to claim 12 wherein said polymer matrix is exposed to one suspension comprising particles comprising silver and particles comprising palladium and gold.

15. The method according to claim 12 further comprising exposing said polymer matrix to a primer before exposing said polymer matrix to the at least one suspension comprising metal particles.

16. An article comprising a polymer matrix according to claim 1.

17. The article according to claim 16, wherein said article is selected from the group consisting of a medical device, a catheter, an endotracheal tube, a stent, a graft, a stent graft, a chromatography gel, a filter, an air filter, a water filter, a wound dressing, a mesh, a degradable bone fixation plug or screw, a degradable ligament implant, a tendon implant, a dental implant, a nerve guide, a medical instrument, a disposable article, a medical disposable article, a contact lens, a pacemaker, a pacemaker electrode, a stent, a dental implant, a rupture net, a rupture mesh, a blood centrifuge equipment, a surgical instrument, a glove, a blood bag, an artificial heart valve, a central venous catheter, a peripheral venous catheter, a vascular port, a haemodialysis equipment, a peritoneal dialysis equipment, a plasmapheresis device, an inhalation drug delivery device, a vascular graft, an arterial graft, a cardiac assist device, a wound dressing, an intermittent catheter, an ECG electrode, a peripheral stent, a bone replacing implant, an orthopaedic implant, an orthopaedic device, a tissue replacing implant, an intraocular lens, a suture, a needle, a drug delivery device, an endotracheal tube, a shunt, a drain, a suction device, and a hearing aid device.

18. The polymer matrix according to claim 1, wherein the metal particles have an average particle diameter of from about 100 to about 600 Å.

* * * * *